US011810299B1

(12) United States Patent
Huet et al.

(10) Patent No.: US 11,810,299 B1
(45) Date of Patent: Nov. 7, 2023

(54) METHOD AND SYSTEM FOR COMPUTER AIDED DIAGNOSIS USING ENSEMBLED 2D AND 3D NEURAL NETWORKS BASED ON MEDICAL IMAGES

(71) Applicant: MEDIAN TECHNOLOGIES, Valbonne (FR)

(72) Inventors: Benoît Huet, Roquefort-les Pins (FR); Danny Francis, Antibes (FR); Pierre Baudot, Marseilles (FR)

(73) Assignee: MEDIAN TECHNOLOGIES, Valbonne (FR)

( * ) Notice: Subject to any disclaimer, the term of this patent is extended or adjusted under 35 U.S.C. 154(b) by 0 days.

(21) Appl. No.: 18/351,699

(22) Filed: Jul. 13, 2023

(30) Foreign Application Priority Data

Jul. 15, 2022 (EP) .................................... 22315156

(51) Int. Cl.
*G06T 7/00* (2017.01)
*G06V 10/25* (2022.01)
(Continued)

(52) U.S. Cl.
CPC .............. *G06T 7/0012* (2013.01); *G06T 7/73* (2017.01); *G06V 10/25* (2022.01); *G06V 10/26* (2022.01); *G06V 10/32* (2022.01); *G06V 10/774* (2022.01); *G06V 10/776* (2022.01); *G06V 10/82* (2022.01); *G16H 50/20* (2018.01);
(Continued)

(58) Field of Classification Search
CPC ..... G06T 7/0012; G06T 7/73; G06T 2200/04; G06T 2207/10081; G06T 2207/10088; G06T 2207/20081; G06T 2207/20084; G06T 2207/30096; G06V 10/25; G06V 10/26; G06V 10/32; G06V 10/774; G06V 10/776; G06V 10/82; G06V 2201/03; G16H 50/20
See application file for complete search history.

(56) References Cited

U.S. PATENT DOCUMENTS 9,934,364 B1 4/2018 Kumar et al.
11,701,066 B2 * 7/2023 Yan .......................... G06F 18/21
382/131

(Continued)

OTHER PUBLICATIONS

Venkadesh et al., "Deep Learning for Malignancy Risk Estimation of Pulmonary Nodules Detected at Low-Dose Screening CT", Radiology, vol. 300, No. 2, Aug. 1, 2021, pp. 438-447.
Wang et al., "Central focused convolutional neural networks: Developing a data-driven model for lung nodule segmentation", Medical Image Analysis, Oxford University Press, Oxford, GB, vol. 40, Jun. 30, 2017, pp. 172-183.

(Continued)

*Primary Examiner* — Siamak Harandi
(74) *Attorney, Agent, or Firm* — HAUPTMAN HAM, LLP

(57) ABSTRACT

A method for generating a machine learning model for characterizing a plurality of Regions Of Interest ROIs based on a plurality of 3D medical images and an associated method for characterizing a Region Of Interest ROI based on at least one 3D medical image. The methods proposed here aim to provide complementary strategies to enable a classification of ROIs from 3D medical images which could take profit of the advantageous and complementarity of both 2D and 3D CNNs to improve the accuracy of the prediction. More precisely, the present disclosure proposes a 2D model that complements the 3D model so that the sensitivity/specificity of the diagnosis is improved by taking advantage of complementary notions.

27 Claims, 3 Drawing Sheets

(51) Int. Cl.
  *G06V 10/26* (2022.01)
  *G06V 10/774* (2022.01)
  *G06V 10/82* (2022.01)
  *G06T 7/73* (2017.01)
  *G06V 10/32* (2022.01)
  *G06V 10/776* (2022.01)
  *G16H 50/20* (2018.01)

(52) U.S. Cl.
  CPC .............................. *G06T 2200/04* (2013.01); *G06T 2207/10081* (2013.01); *G06T 2207/10088* (2013.01); *G06T 2207/20081* (2013.01); *G06T 2207/20084* (2013.01); *G06T 2207/30096* (2013.01); *G06V 2201/03* (2022.01)

(56) References Cited

U.S. PATENT DOCUMENTS

| | | | |
|---|---|---|---|
| 2020/0027207 A1* | 1/2020 | Zhang | G06F 18/2135 |
| 2020/0160997 A1 | 5/2020 | Bagci et al. | |
| 2021/0225511 A1 | 7/2021 | Kiraly et al. | |

OTHER PUBLICATIONS

Setio et al., "Pulmonary Nodule Detection in CT Images: False Positive Reduction Using Multi-View Convolutional Networks", IEEE Transactions On Medical Imaging, vol. 35, No. 5, May 1, 2016, pp. 1160-1169.

Xie et al., "Automated Pulmonary nodule detection in CT images using deep convolutional neural networks", Pattern Recognition, Elsevier, GB, vol. 85, Aug. 3, 2018, pp. 109-119.

Halder et al., "Lung Nodule Detection from Feature Engineering to Deep Learning in Thoracic CT Images: a Comprehensive Review", Journal of Digital Imaging, Springer International Publishing, Cham, vol. 33, No. 3, Jan. 29, 2020, pp. 655-677.

Riquelme et al., "Deep Learning for Lung Cancer Nodules Detection and Classification in CT Scans", AI, vol. 1, No. 1, Jan. 8, 2020, pp. 28-67.

Extended European Search Report issued in corresponding European Application No. 22315156.4, dated Jan. 5, 2023, pp. 1-10, European Patent Office, Munich, Germany.

Riquelme et al., "Deep Learning for Lung Cancer Nodules Detection and Classification in CT Scans", AI, vol. 1, No. 1, Jan. 8, 2020, pp. 28-67.

* cited by examiner

METHOD AND SYSTEM FOR COMPUTER AIDED DIAGNOSIS USING ENSEMBLED 2D AND 3D NEURAL NETWORKS BASED ON MEDICAL IMAGES

TECHNICAL FIELD

The disclosure relates broadly to methods and systems for Computer Aided Diagnosis (CAD) based on 3-dimensional medical images.

The invention more particularly relates to a machine learning model for characterizing ROIs in 3-dimensional medical images.

BACKGROUND

Diagnosing diseases of internal organs without any invasive procedure has been possible thanks to medical imaging. In particular in 1967, Godfrey Hounsfield had the idea of computed tomography that allows us today to take 3D medical images of the inner body of patients. Since then, 3D medical imaging has been widely used to help clinicians to diagnose diseases such as cancers.

The problem with those 3D images is that they are usually voluminous and would take long time to be read by the radiologists. Hence, computer aided diagnosis (CAD) becomes important as to help improve productivity and improve the diagnostic performance of radiologists in their image interpretation, and in particular in the context of screening programs like the National Lung Screening Trial in the US. In 2012, at the ImageNet Large Scale Visual Recognition Challenge, a deep neural network outclassed all other traditional models. That triggered a revolution in the image processing community, as they had to acknowledge that deep learning was much more efficient than methods at use at that time.

It is known that the approach based on 2D CNNs is usually short of estimating the malignancy of lung nodules as the application of 2D CNNs for nodule characterization (CADx) has been limited to 2D space thus falling short of incorporating vital contextual and volumetric information. To overcome such drawback, it is proposed in patent publication no. US 2021/0225511 A1 entitled "Method and system for improving cancer detection using deep learning", and also in patent publication no. US 2020/0160997 A1 entitled "Method for detection and diagnosis of lung and pancreatic cancers from imaging scans" a completely 3D deep neural network architecture designed to detect lung nodules in order to appreciate the 3D nature of the nodule shape.

However, 3D CNNs has limitations for which the 2D CNNs are much less affected. For example, 3D CNNs require much larger dataset to process and train the neural network (where 2D samples are agglomerated) and are more likely to overfitting, thus prohibiting neural network to have sufficiently deep architecture.

To overcome such drawbacks, it is proposed in "Venkadesh" (See Venkadesh et al, *"Deep Learning for Malignancy Risk Estimation of Pulmonary Nodules Detected at Low-Dose Screening CT"*, published in Radiology, 2021 August; 300(2):438-447) to use an ensemble of 2D and 3D CNNs being trained independently in order to analyze multiple patches of nodules and to characterize the malignancy of lung lesions using deep models.

However, in Vankadesh's combined strategy (of 2D and 3D models), the 2D model is configured by modeling multiple independent 2D networks whose input are different 2D rotation views of each of the ROIs (See "Setio et al.", *"Pulmonary nodule detection in CT images: false positive reduction using multi-view convolutional networks"*, published in IEEE Trans Med Imaging, 2016 May; 35(5):1160-1169). As medical images are generally highly anisotropic, it means that the voxel spacing along the x-axis, the y-axis and the z-axis are different from each other. So taking different rotation views for each ROI as proposed in Venkadesh, will cause different resolution along the different axes, which has to be compensated by preliminary resampling operation. A major disadvantage of the resampling operation is that it is based on assumptions about what the image looks like between slices while these assumptions may be false and not faithful to the original data.

Note furthermore that the solution of Venkadesh suffers not only from altered information due to the resampling operation especially in the case of small findings (such as early-stage malignant lung nodules), but also from the loss of information due to the partial covering of the ROIs which filters out ROIs' relevant information for classification.

Indeed, as each of the 2D models of Venkadesh (or Setio) is trained only on one single orientation (one single rotation view), the effective available sample size is further divided, thus making the training dataset to a quite limited number of images, failing to obtain invariant representation of findings and producing fairly poor model generalizability from design perspective.

A desirable approach would be to make predictions of diagnosis scores based on the as-comprehensive-as possible information from the 3D images with a consecutive analysis by the neural network which will represent such information in an invariant manner.

There is thus a need for a method for Computer Aided Diagnosis (CAD) based on 3-dimensional medical images that improves the sensitivity/specificity of the diagnosis and/or the "Area Under the Curve" (AUC) of "Receiver Characteristic Operator" (ROC) scores.

More particularly, there is a need for a method for Computer Aided Diagnosis based on 3-dimensional medical images that:

Provides robust prediction, and/or
Improve AUC-ROC score of the prediction, and/or
Covers each nodule as a whole, and/or
Obtain invariant representation of nodules, and/or
Takes consideration of small and large nodules as well.

SUMMARY

According to a first aspect, disclosed is a method for generating a machine learning model for characterizing a plurality of Regions Of Interest ROIs based on a plurality of 3D medical images, comprising the steps of:

Providing said plurality of 3D medical images and
Localizing a plurality of ROIs in said plurality of 3D medical images, and for each ROI, defining a 3D bounding box by a set of 6 extreme coordinates (Xmin, Xmax,Ymin,Ymax,Zmin,Zmax), and
On one hand:
For each defined 3D bounding box, 2D preprocessing in order to extract a plurality of Ki 2D patches from each ROI comprised in said 3D bounding box, and
Training a 2D machine learning model based on the extracted 2D patches,
On the other hand:
For each defined 3D bounding box, 3D preprocessing in order to extract at least one 3D patch from each ROI comprised in said 3D bounding box, and Training a 3D machine learning model for characterizing said plurality of ROIs based on the extracted 3D patches for the plurality of ROIs, wherein the step of 2D preprocessing comprises at least extracting a plurality of Ki 2D patches as contiguous and parallel slices with respect to a single predetermined plane, and wherein the 2D machine learning model is configured to be trained for characterizing the plurality of ROIs based on the extracted plurality of 2D patches for the plurality of ROIs.

In some examples, each 2D patch of the plurality of Ki 2D patches are obtained without any resampling.

In some examples, said single predetermined plane is parallel to one of the following three planes: the sagittal plane, the coronal plane and the axial plane, and preferably be parallel to the plane having the best resolution, and further preferably parallel to the axial plane.

In some examples, said step of 2D preprocessing further comprises, before said step of extracting a plurality of Ki 2D patches, a step of extracting 2D ROI coordinates by calculating coordinates of centers of each ROI in axial view of each bounding box (Xmin,Xmax,Ymin,Ymax,Zmin,Zmax), with each center being defined for example by coordinates ((Xmin+Xmax)/2, (Ymin+Ymax)/2), for all Z in [Zmin, Zmax]. Said step of extracting a plurality of Ki 2D patches may comprise cropping, contiguously along the z-axis, a plurality of 2D patches of dimensions P×Q, for example with P=Q=64.

In some examples, said step of 2D preprocessing further comprises a step of 2D voxel values normalization, this latter being implemented before or after said step of extracting a plurality of Ki 2D patches.

In some examples, said step of 3D preprocessing:
comprises a step of extracting at least one 3D patch of each ROI, and
prior to the step of extracting at least one 3D patch of each ROI, further comprises a step of extracting 3D ROI coordinates by calculating the coordinates of center of each ROI, with each ROI center being for example defined by coordinates ((Xmin+Xmax)/2, (Ymin+Ymax)/2, (Zmin+Zmax)/2). The step of extracting at least one 3D patch may comprise cropping, around the center coordinates of each ROI, a 3D patch of dimensions P×Q×R, for example with P=Q=R=64. Otherwise, said 3D preprocessing step may further comprise a step of 3D voxel values normalization, this latter being implemented before or after said extracting step. Furthermore, said step of 3D preprocessing may further comprise, before said step of extracting at least one 3D patch, a step of 3D volume resampling of each 3D image wherein a ROI has been localized.

In some examples, the step of 2D training comprises:
an initialization step of said 2D machine learning model, and
a continued training step of said 2D machine learning model.

With said 2D machine learning model being designed for computing diagnosis score based on one 2D patch, the initialization step may comprise initializing weights of said 2D machine learning model based on at least one among random determination of said weights and predetermined weights. In addition or as an alternative, the continued training step may comprise:

i. for each mini-batch of all the extracted patches of the plurality of ROIs, a computing step of diagnosis score using 2D machine learning model, wherein the mini-batch is selected randomly, ii. for each previously computed diagnosis score, a computing step of error estimation made by the 2D machine learning model, iii. an updating step of the weights using a gradient-based method, iv. repeating steps i. to iii. until a predefined stopping condition is reached, thus achieving a trained 2D machine learning model with optimized weights.

In some examples, the 3D training step comprises:
an initialization step of said 3D machine learning model, and
a continued training step of said 3D machine learning model.

With said 3D machine learning model being designed for computing diagnosis score based on one 3D patch, the initialization step may comprise initializing weights of said 3D machine learning model based on at least one among random determination of said weights and predetermined weights. In addition or as an alternative, the continued training step may comprise:

i. for each mini-batch of all the extracted patches of the plurality of ROIs, a computing step of diagnosis score using 3D machine learning model, wherein the mini-batch is selected randomly, ii. for each previously computed diagnosis score, a computing step of error estimation made by the 3D machine learning model, iii. an updating step of the weights using a gradient-based method, iv. repeating steps i. to iii. until a predefined stopping condition is reached, thus achieving a trained 3D machine learning model with optimized weights.

In some examples, each training step may further be performed on morphological and/or radiomics features. Said morphological features may comprise at least baseline features. Said baseline features may comprise at least one among:
a volume of said at least one anatomical structure,
an elongation of said at least one anatomical structure,
a min and/or max size of oriented bounding boxes of said at least one anatomical structure, and
an HPI mean of said at least one anatomical structure.

In some examples, the method according to the first aspect of the invention may further comprise:
providing clinical information about each patient, and wherein each training step is further performed on patients clinical information.

According to a second aspect, disclosed is a method for characterizing a Region Of Interest ROI based on at least one 3D medical image, comprising the steps of:
Providing said at least one 3D medical image, and
Localizing one ROI as candidate ROI in said at least one 3D medical image, and
For candidate ROI, defining one candidate 3D bounding box by a set of 6 extreme coordinates (Xmin,Xmax, Ymin,Ymax,Zmin,Zmax), and
On one hand:
For the candidate 3D bounding box, 2D preprocessing in order to extract a plurality of candidate 2D patches from the candidate ROI comprised in the candidate 3D bounding box, and Implementing a trained 2D machine learning model configured for characterizing the candidate ROI, On the other hand:

For the candidate 3D bounding box, 3D preprocessing in order to extract at least one candidate 3D patch from the candidate ROI comprised in the candidate 3D bounding box, and Implementing a trained 3D machine learning model configured for characterizing the candidate ROI based on at least one extracted candidate 3D patch, then Ensembling a plurality of 2D diagnosis scores provided by said trained 2D machine learning model (the output by implementing said 2D machine learning model) and a plurality of 3D diagnosis score provided by said trained 3D machine learning model (the output by implementing said 3D machine learning model) in order to output one overall score per said candidate ROI, wherein the step of 2D preprocessing comprises at least extracting a plurality of K candidate 2D patches as contiguous and parallel slices with respect to a single predetermined plane, and wherein the step of implementing the trained 2D machine learning model is performed based on the extracted plurality of candidate 2D patches.

The scoring achieved by implementing the above introduced method takes advantage that the method is based on extracted 2D slices which are faithful to the original data and thus does not fail to reflect the reality in this respect.

It is thus proposed a method for Computer Aided Diagnosis based on 3-dimensional medical images that improves the sensitivity/specificity of the diagnosis and/or the "Area Under the Curve" (AUC) of "Receiver Characteristic Operator" (ROC) scores.

More particularly, it is thus proposed a method for Computer Aided Diagnosis based on 3-dimensional medical images that:

Provides robust prediction, and/or

Covers each ROI as a whole, and/or

Takes consideration of small and large ROIs as well.

In some examples, said trained 2D and 3D machine learning models have been trained by implementing a method for generating a machine learning model according to the first aspect of the invention.

In some examples, said single predetermined plane is parallel to one of the following three planes: the sagittal plane, the coronal plane and the axial plane, and preferably be parallel to the plane having the best resolution, and further preferably parallel to the axial plane.

In some examples, said step of 2D preprocessing further comprises, before said step of extracting a plurality of K candidate 2D patches, a step of extracting 2D ROI coordinates by calculating coordinates of centers of the candidate ROI in axial view of the candidate 3D bounding box (Xmin,Xmax,Ymin,Ymax,Zmin,Zmax), with each center being defined for example by coordinates ((Xmin+Xmax)/2, (Ymin+Ymax)/2), for all Z in [Zmin, Zmax]. Said step of extracting a plurality of K candidate 2D patches may comprise cropping, contiguously along the z-axis, a plurality of K candidate 2D patches of dimensions P×Q, for example with P=Q=64. Said plurality of Ki 2D patches may thus be comprised, or constituted, of a plurality of P×Q 2D patches for each 3D bounding box, preferably each plurality of P×Q 2D patches being constituted of Ki=Zmax-Zmin patches.

In some examples, said step of 2D preprocessing further comprises a step of 2D voxel values normalization, this latter being implemented before or after said step of extracting a plurality of K candidate 2D patches.

In some examples, said step of 3D preprocessing:

comprises a step of extracting at least one candidate 3D patch of the candidate ROI, and prior to the step of extracting at least one candidate 3D patch of the candidate ROI, further comprises a step of extracting 3D ROI coordinates by calculating the coordinates of center of the candidate ROI, with the candidate ROI center being for example defined by coordinates ((Xmin+Xmax)/2, (Ymin+Ymax)/2, (Zmin+Zmax)/2). The step of extracting at least one candidate 3D patch may comprise cropping, around the center coordinates of the candidate ROI, a candidate 3D patch of dimensions P×Q×R, for example with P=Q=R=64. In addition or as an alternative, said step of 3D preprocessing may further comprise a step of 3D voxel values normalization, this latter being implemented before or after said step of extracting at least one candidate 3D patch of the candidate ROI. In addition or as an alternative, said step of 3D preprocessing may further comprise, before said step of extracting at least one candidate 3D patch of the candidate ROI, a 3D volume resampling of each 3D image wherein the candidate ROI has been localized.

In some examples, the step of implementing the trained 2D machine learning model is performed N times based on the plurality of K extracted candidate 2D patches in order to compute, each time, K candidate diagnosis scores for one candidate ROI, thus achieving K candidate 2D diagnosis scores for each one series of N series.

In some examples, the step of implementing the trained 3D machine learning model is performed M times based on the at least one extracted candidate 3D patch in order to compute each time at least one candidate diagnostic score for one candidate ROI, thus achieving at least one candidate 3D diagnosis scores for each series of M series. The step of ensembling may comprise:

a step of max-pooling the N series of K candidate 2D diagnosis scores as computed for said plurality of extracted candidate 2D patches, with said step of max-pooling comprising, for each series j of said N series of K candidate 2D diagnosis scores, a step of generating one maximum candidate 2D diagnosis score Sj by selecting, from said K candidate 2D diagnosis scores, the diagnosis score having the maximum value thus achieving one candidate maximum 2D diagnosis score per series for N series, wherein the trained 2D machine learning model used for each series j of said N series is different from each other, preferably having different weights, and a step of pooling the M series of least one candidate 3D diagnosis scores for each ROI as computed for said at least one extracted candidate 3D patch. Furthermore, the step of ensembling may further comprise a step of outputting one overall score per said candidate ROI by pooling N 2D diagnostic scores of step and M 3D diagnostic scores of step together.

In some examples, the method according to the second aspect of the invention may further comprise a step of, for the candidate ROI, extracting morphological features of said ROI based on 3D medical image and by using morpho-radiomics features extractors. Said morphological features may comprise baseline features. Said baseline features may comprise at least one among:

a volume of at least one anatomical structure, an elongation of at least one anatomical structure, a min and/or max size of oriented bounding boxes of at least one anatomical structure, and an HPI mean of at least one anatomical structure.

According to either the first aspect of the invention or the second one, the 3-dimensional medical images may comprise Computed Tomography (CT) images or Magnetic Resonance Imaging (MRI) images.

A further aspect of the present disclosure relates to a non-transitory computer readable medium storing instructions which, when implemented by at least one digital processing device, performs at least the steps of the method according the first aspect of the invention and/or the steps of the method according the second aspect of the invention.

A further aspect of the present disclosure relates to a computer program product comprising instructions which, when implemented by at least one digital processing device, performs at least the steps of the method according the first aspect of the invention and/or the steps of the method according the second aspect of the invention.

Other objects, features and advantages of the invention(s) disclosed herein, and their various embodiments/aspects, may become apparent in light of the description of some exemplary embodiments that follows.

BRIEF DESCRIPTION OF THE DRAWINGS

Reference will be made in detail to embodiments of the disclosure, non-limiting examples of which may be illustrated in the figures of the accompanying drawings. Some figures may be in the form of diagrams. Some elements in the figures may be exaggerated; others may be omitted, for illustrative clarity.

Any text (legends, notes, reference numerals and the like) appearing on the drawings are incorporated herein by reference.

DETAILED DESCRIPTION

Figure 1:
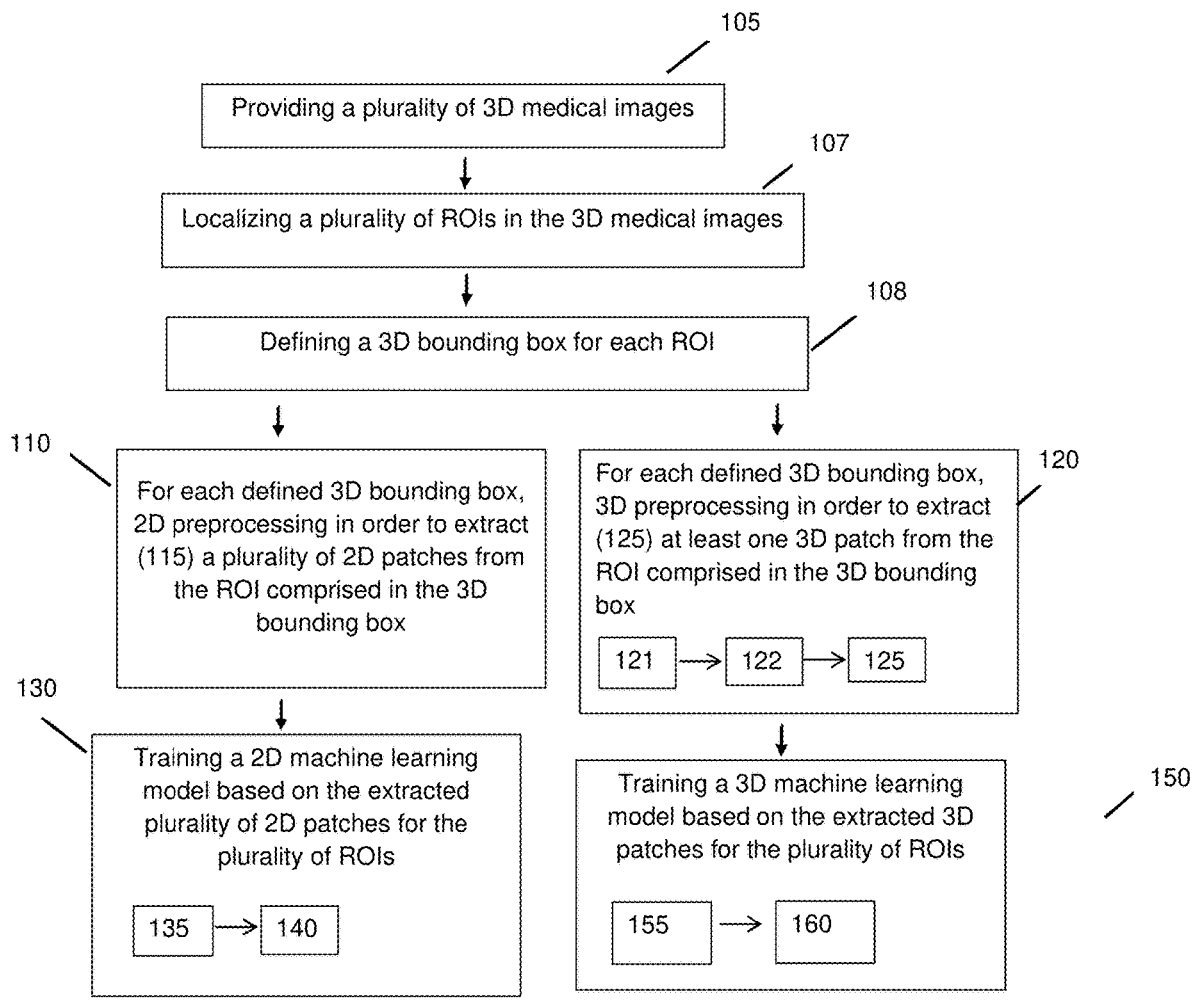
FIG. 1 is a flowchart according to some examples of the method according to the first aspect of the present disclosure.

A "finding" may be defined as lesion, consolidation, nodule, being malignant or benign, and anything with clinical interest that may help to make a diagnosis.

A Region Of Interest (ROI) may be defined as a subpart of a 3D image, more precisely a subset of the voxels of a 3D image that covers a particular type of tissue such as organ, lesion, consolidation, nodule, being malignant or benign, and anything with clinical interest that may help to make a diagnosis. A ROI may cover the whole 3D image if the whole image is considered as of interest and relevant for diagnosis. In the context of the present disclosure, "ROI" is interchangeable with the term "finding".

A bounding box may be defined as a minimal rectangular cuboid including a ROI. A bounding box may comprise all voxels of a 3D image. In the context of the present disclosure, one bounding box contains one ROI. In other words, one ROI corresponds to at least one bounding box.

An axial plane may be defined as a transverse plane at right angles to the long axis of the body, as in CT scanning and MRI scanning.

In the context of the present disclosure, contiguous patches or slices mean that they are next or adjacent to each other in sequence.

As mentioned above, 2D CNNs and 3D CNNs have different limitations. As a result, the architecture and moreover the representation encoded in 2D and 3D networks for a given problem have to be conceived in very different manners.

However, the fact of combining 2D CNNs and 3D CNNs by designing a system for either models (2D and 3D) would not be enough to address the drawbacks of both models. For example, the solution of Venkadesh combining 2D and 3D models, still fails to address the limitations in 3D CNNS by its 2D model but rather introduces further problems such as the loss and alteration of information induced by its patch-extraction method inevitably including a resampling operation as used in the 3D model and the limited sample size for training the 2D model.

The disclosure proposed here aims to provide complementary strategies to enable a classification of ROIs from 3D medical images which could take profit of the advantageous and complementarity of both 2D and 3D CNNs to improve the accuracy of the prediction.

More precisely, the present disclosure proposes a 2D model that complements the 3D model so that the sensitivity/specificity of the diagnosis is improved by taking advantage of complementary notions at least in the following aspects:

i) 2D Preprocessing and 3D Preprocessing

Usually, a 3D pre-processing module is more informative but the accuracy is comprised for reasons explained above especially due to artificial assumption made during the resampling (by the interpolation operation).

Different from its counterpart, a 2D preprocessing module is less informative but is more faithful about the original data. However, in some 2D models such as the one in Venkadesh and Setio, as a resampling will be required during the preprocessing given its extraction method of the 2D views, it is likely to suffer comprised faithfulness due to the resampling and partial information about the 3D images.

The present disclosure allows obtaining as-comprehensive-as possible information from the 3D images with a consecutive analysis by the neural network which will represent such information in an invariant manner thanks to its 2D model and in particular, by extracting a plurality of contiguous and parallel slices for each ROI in a predetermined plane with a better resolution. In the present extraction used in the 2D model, no resampling will be required. Furthermore, the whole nodule and both small and large sized nodules are taken into account by the present solution.

ii) Diagnosis with the Trained 2D Model

The extraction method proposed by the present disclosure allows extracting a plurality of K 2D patches for one ROI for diagnosis, and the input of this plurality of K 2D patches to a trained 2D model would yield K diagnosis scores, so that a highest score can be selected among said K scores where the highest score has more chance of being cancerous (the nodule having the highest risk of malignancy).

iii) Ensembling 2D and 3D Models to Calculate the Overall Score: Pooling all the Scores Calculated from the 2D and 3D Models to Calculate the Overall Score Assuming a low-value score "0" indicates low risk and a high-value score "1" indicates high risk, a mid-range score (for example 0.4-0.6) will indicate uncertainty of prediction.

In case where there are numerous high or low values and some mid values, in order to highlight the high or low value while reducing the uncertainty, the invention proposes to pool all the scores. Pooling methods do not restrict however to averaging scores, as it can also be profitable to use other methods to derive one score from the 2D and 3D scores (e.g. XGBoost, weighted averages, etc.).

Therefore, it is advantageous of the claimed method of training a machine learning for characterizing ROIs and using the trained machine learning model for the same purpose, by configuring how to choose the 2D images as 2D model input in the 3D volume and of the subsequent 2D network structure to further aggregate them into a single volume prediction is nonetheless fully open but also critical to obtain an accurate result.

More particularly, advantages of the present disclosure may be:
 Provides robust prediction, and/or
 Improve AUC-ROC score of the prediction, and/or
 Covers each ROI as a whole, and/or
 Obtain invariant representation of nodules, and/or
 Takes consideration of small and large ROIs as well.

FIG. 1 shows a flowchart of an embodiment of the first aspect of the present invention.

According to its first aspect, the invention provides a method 100 for generating a machine learning model for characterizing a plurality of Regions Of Interest (ROIs) based on a plurality of 3D medical images.

The applications of characterizing ROIs may be the classification of severity of a disease, making a decision of whether the ROI is benign or malignant based on a deterministic score or other factors, or making a decision of a pathological status.

Whilst the applications of the present disclosure are discussed in the context of calculating diagnostic score (such as malignant score), it will be appreciated that the applications may be extended to those other than diagnostic score, such as the classification of severity of a disease.

It is to be appreciated that whilst the applications are disclosed in the context of liver fibrosis and lung nodule, a disease in the context of the present disclosure, may manifest in a defined anatomical structure, and may not be limited to tumor, be it cancerous or not, neither be limited to liver or lung.

The method 100 comprises the steps of:
 Providing 105 said plurality of 3D medical images and
 Localizing 107 a plurality of ROIs in said plurality of 3D medical images, and for each ROI, defining 108 a 3D bounding box by a set of 6 extreme coordinates (Xmin, Xmax,Ymin,Ymax,Zmin,Zmax).

The provided 105 3D medical images may comprise Computed Tomography (CT) images or Magnetic Resonance Imaging (MRI) images.

In the context of the present disclosure, one 3D image may contain 0, 1 or several ROIs. Being provided with a plurality of 3D medical images, a plurality of ROIs may be localized 107.

The localization 107 of ROIs may be realized automatically, for example by CADe, or manually, for example by a clinician.

In some examples, the localization 107 of a ROI may comprise segmenting at least one determined anatomical structure of a patient in each image of the plurality of 3D medical images and defining the implied mask of said at least one anatomical structure as a ROI.

In some examples, the localization 107 of a ROI may advantageously be limited to said at least one determined anatomical structure. The method 100 may further comprise a step of determining if a localized ROI is inside of said at least one determined anatomical structure. In order to determine if a localized ROI is inside of said at least one determined anatomical structure, it may be envisaged to compute the rate between the volume of the intersection of the bounding box and the lung mask and the volume of the bounding box. In some examples, if the rate equals to or is larger than 0.5, then it is considered the localized ROI is inside of said determined anatomical structure. The rate may vary depending on the anatomical structure, the application of the localization and other factors. In some examples, the method may further comprise a step of keeping only the localized ROIs which have been determined to be inside of said determined anatomical structure.

On one hand, the method 100 further comprises the following steps:
 For each defined 3D bounding box, 2D preprocessing 110 in order to extract a plurality of 2D patches from the ROI comprised in said 3D bounding box, and
 Training 130 a 2D machine learning model based on the extracted plurality of 2D patches.

On the other hand, the method 100 further comprises the following steps:
 For each 3D bounding box, 3D preprocessing 120 in order to extract at least one 3D patch from each ROI comprised in said 3D bounding box, and
 Training 150 a 3D machine learning model for characterizing said plurality of ROIs based on the extracted 3D patches for the plurality of ROIs.

Figure 4:
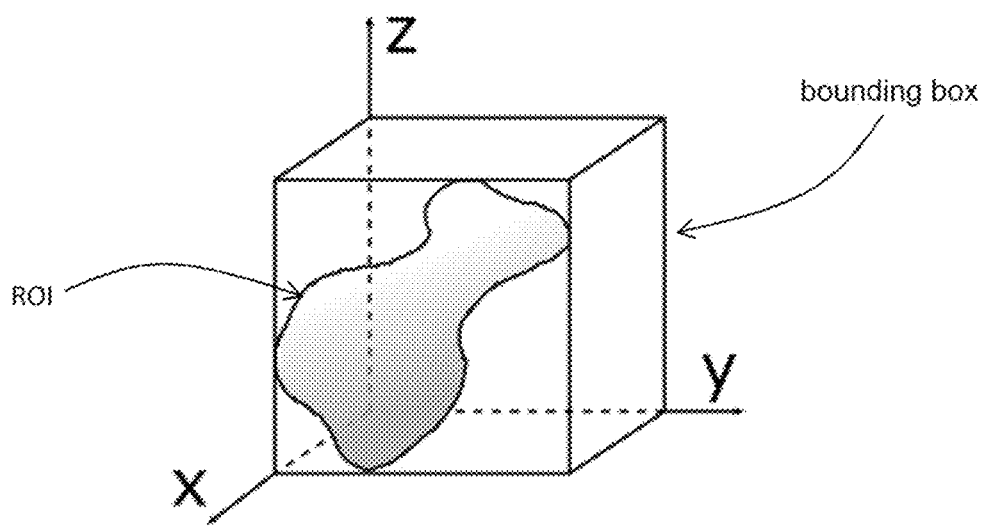
FIG. 4 shows an example of a nodule inside of a bounding box.

For exemplary purpose, it is shown in FIG. 4 a ROI in a bounding box. In the context of the present disclosure, each bounding box contains one ROI. For purpose of understanding, the bounding box is denoted by a set of 6 extreme coordinates (Xmin,Xmax,Ymin,Ymax,Zmin,Zmax). It is to be appreciated that other coordinates can be also used as long as they are applicable in a 3D X,Y,Z coordinates system.

Advantageously, the method 100 is such that, for each defined 3D bounding box, the step of 2D preprocessing 110 comprises at least extracting 115 a plurality of Ki 2D patches (for each ROI i) as contiguous and parallel slices with respect to a single predetermined plane.

Each 2D patch of the plurality of Ki 2D patches are obtained without any resampling. This way the extracted 2D patches can not only cover the integrality of the original data, but also reflect the reality without providing altered information caused by the resampling operation.

Preferably, said single predetermined plane is parallel to one of the following three planes: the sagittal plane, the coronal plane and the axial plane. More preferably, said single predetermined plane is parallel to the plane having the best resolution. Further preferably, said single predetermined plane is parallel to the axial plane.

Figure 3:
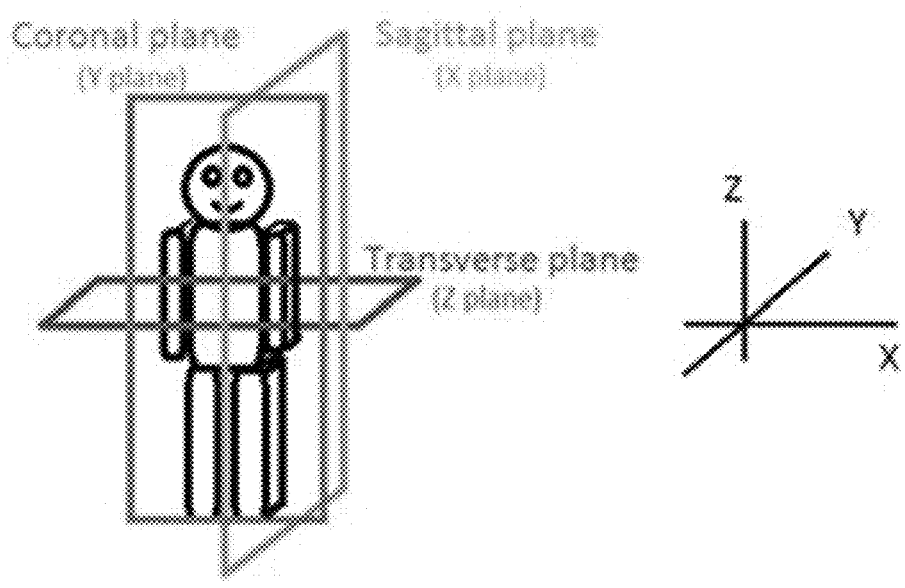
FIG. 3 shows anatomical planes and body axes (X-axis, Y-axis, Z-axis)

FIG. 3 shows anatomical planes and body axes (X-axis, Y-axis, Z-axis).

Referring to FIG. 3, it is illustrated a sagittal plane (X plane), a coronal plane (Y plane) and a Transverse plane (Z plane). Each of these three planes contains two of the three coordinate axes (X,Y,Z) in the three-dimensional coordinate system. For example, the plane that contains X-axis and Y-axis is the axial plane called XY plane (not marked in the drawing) or Z plane.

As shown in FIG. 3, an axial plane is perpendicular to the long axis (Z-axis), i.e. spine of the body (head, neck, trunk, tail).

Axial plane can be interchangeable with transverse plane in the context of the present disclosure.

A Sagittal Plane runs from front to back, dividing the body into right and left parts. A coronal plane runs from side to side, dividing the body into anterior and posterior portions.

In some examples, the 2D slices are extracted with respect to the same predetermined plane. In some further examples, the same predetermined plane is parallel to the axial plane with the best resolution. The ROI is extracted in the plane with the best resolution, may be understood in the context of the present disclosure that the ROI may be better depicted by axial viewed patches.

This approach allows taking into consideration of morphological characteristic of the nodules (ROIs) and may be particularly advantageous in the case of small spiculated nodules.

Furthermore, this approach allows taking into consideration of the nodule size and may be particularly advantageous in the case of large nodules as the extraction allows covering of the whole nodule.

This way not only the extracted 2D patches cover the integrality of the original data, but also the extracted 2D patches can reflect the reality since they are obtained without any resampling. The as-comprehensive-as-possible and faithful extraction of the 3D medical image to be used to train the 2D machine learning model helps to improve the AUC-ROC score of the model.

Said step of 2D preprocessing 110 may further comprise, before said step of extracting 115 a plurality of Ki 2D patches, a step of extracting 111 2D ROI coordinates by calculating coordinates of centers of each ROI in axial view of each bounding box (Xmin,Xmax,Ymin,Ymax,Zmin,Zmax), with each center being defined for example by coordinates ((Xmin+Xmax)/2, (Ymin+Ymax)/2), for all Z in [Zmin, Zmax]. Thus, for each ROI, each plurality of Ki 2D patches may comprise as Ki=Zmax-Zmin+1 patches.

More specifically, said step of extracting 115 a plurality of Ki 2D patches may comprise cropping, contiguously along the Z-axis, a plurality of 2D patches of dimensions P×Q, for example with P=Q=64.

Said plurality of Ki 2D patches is thus comprised, or constituted, of a plurality of Ki 2D patches of dimensions P×Q for each 3D bounding box.

If needed, said step of 2D preprocessing 110 may further comprise a step of 2D voxel values normalization 113. This normalization step 113 may be implemented before or after said step of extracting 115 a plurality of Ki 2D patches and/or may concern normalization of luminance attenuation (HU) of the concerned pixels or voxels. More particularly, the step of 2D voxel values normalization 113 may involve a clip of values of voxels (or pixels since we talk about 2D patches) between two predefined minimal and maximal values, then a transformation by applying a predefined affine function to the values of voxels of the 2D patches. If step 115 is implemented before step 113, then step 112 only needs to be applied on the 3D image form which the Ki 2D patches are to be extracted 115. If step 113 is implemented before step 115, then it is necessary to normalize the luminance attenuation (HU) on all 2D patches.

Thus, following the step of extracting 115 a plurality of Ki 2D patches, a plurality of normalized Ki 2D patches may be achieved which may be used for 2D training 130 of said 2D machine learning model.

As previously mentioned and further advantageously, the method 100 is such that the 2D machine learning model is trained based on the extracted plurality of Ki 2D patches for the plurality of ROIs, that is, a plurality of 2D patches are used to train the 2D machine learning model.

This way the sampling size is increased, leading to the improved accuracy of the trained machine learning model as well as to the improved model robustness, notably with an synergic effect in combination with the specific manner according to which the step of 2D preprocessing 110 is performed, thus leading to further improvement of the accuracy of the trained model.

The step of 2D training 130 may comprise:
 an initialization step 135 of said 2D machine learning model, and
 a continued training step 140 of said 2D machine learning model In some examples, the initialization step 135 may comprise initializing weights of said 2D machine learning model based on at least one among random determination of said weights and predetermined weights.

The continued training step 140 may comprise:
 i. for each mini-batch of all the extracted patches of the plurality of ROIs, a computing step 141 of diagnosis score using 2D machine learning model, wherein the mini-batch is selected randomly,
 ii. for each previously computed diagnosis score, a computing step 142 of error estimation made by the 2D machine learning model,
 iii. an updating step 143 of the weights using a gradient-based method,
 iv. repeating steps 141 to 143 until a predefined stopping condition is reached.

When the predefined stopping condition is reached, the training is terminated.

In some examples, the stopping condition may be reached in at least one of the following situations, the list being non-exhaustive:
 1) after certain number of training;
 2) after reaching certain performance of the model;
 3) if the performance doesn't change, after certain iterations.

Thus a trained 2D machine learning model with optimized weights is achieved.

For implementing the continued training step 140, it may more particularly use a mini-batch gradient descent that is a variation of the gradient descent algorithm that splits the training dataset into small batches that are used to calculate model error and update model coefficients. In some examples, the continued training of the 2D machine learning model may be based on mini-batches.

Note that, among known gradient-based methods, Adam, RMSprop and SGD are methods that can be used for said updating 143 (as well as for the updating 163 detailed below).

We describe below how a trained 3D machine learning model with optimized weights may also be achieved, in a parallel way with respect to the one according to which the trained 2D machine learning model with optimized weights is achieved.

The aforementioned step of 3D preprocessing 120 in order to extract at least one 3D patch from each ROI comprised in said 3D bounding box may:
 comprise a step of extracting 125 at least one 3D patch of each ROI, and
 prior to the step of extracting 125 at least one 3D patch of each ROI, further comprise a step of extracting 121 3D ROI coordinates by calculating the coordinates of center of each ROI. Each ROI center may for example be defined by coordinates ((Xmin+Xmax)/2, (Ymin+Ymax)/2, (Zmin+Zmax)/2).

More particularly, the step of extracting 125 at least one 3D patch may comprise a step of cropping, around the center coordinates of each ROI, a 3D patch of dimensions P×Q×R, for example with P=Q=R=64.

As for said 2D preprocessing step 110, said 3D preprocessing 120 step may further comprise a step of 3D voxel values normalization 123.

The step of 3D voxel values normalization 123 may be implemented before or after said extracting step 125. More particularly, the step of 3D voxel values normalization 123 may involve a clip of values of voxels between two predefined minimal and maximal values, then a transformation by applying a predefined affine function to the values of voxels of the 3D patches.

On the contrary to said 2D preprocessing step 110, the 3D preprocessing step 120 may comprise a step of 3D volume resampling 122 of each 3D image wherein a ROI has been localized 107.

In some examples, step 122 may be implemented before said step of extracting 125 at least one 3D patch.

As explained earlier, the step of 3D volume resampling 122 may be required to solve the problem posed by potential imaging anisotropy and may be configured in order to achieve an isometric spacing. In some examples, a 0.65 mm×0.65 mm×0.65 mm resolution may be achieved respectively in X-axis, Y-axis and Z-axis.

In order to increase the sample size for training the 3D machine learning, the cropped 3D patch may be further processed to generate more than one 3D patches. In some examples, we can crop several patches for one ROI. In one example, the center of the 3D patches can be slightly shifted. In another example, the image can be rotated.

Thus, following the step of extracting 125 at least one 3D patch, a plurality of normalized and resampled 3D patch may be achieved, for the plurality of localized ROIS, with said plurality of normalized and resampled 3D patch being usable for 3D training 150 of said 3D machine learning model.

As for the 2D training 130 of said 2D machine learning model, the 3D training 150 of said 3D machine learning model may comprises:
- an initialization step 155 of said 3D machine learning model, and
- a continued training step 160 of said 3D machine learning model.

In some examples, the initialization step 155 may comprise: initializing weights of said 3D machine learning model based on random determination of said weights or based on predetermined weights.

The continued training step 160 may comprise:
i. for each mini-batch of all the extracted patches of the plurality of ROIs, a computing step 161 of diagnosis score using 3D machine learning model, wherein the mini-batch is selected randomly,
ii. for each previously computed diagnosis score, a computing step 162 of error estimation made by the 3D machine learning model,
iii. an updating 163 step of the weights using a gradient-based method,
iv. repeating steps 161 to 163 until a predefined stopping condition is reached.

Thus a trained 3D machine learning model with optimized weights is achieved.

It is to be understood that, in the context of the present disclosure, examples and explications provided above with regard to step 140 continued training of the 2D machine learning model also applies to step 160 continued training of the 3D machine learning model.

At this stage, a trained 2D machine learning model with optimized weights and a trained 3D machine learning model with optimized weights are thus achieved as a result of said method 100 for generating a machine learning model.

In some examples, the method 100 may comprise extracting morphological features of said ROIs (based on said 2D and/or 3D patches) and by using morpho-radiomics features extractors, for at least one among the training step 130 and the training step 150 to be further performed on morphological and/or radiomics features. Said morphological features comprise at least baseline features, with said baseline features comprising for instance at least one among:
- a volume of said at least one anatomical structure,
- an elongation of said at least one anatomical structure,
- a min and/or max size of oriented bounding boxes of said at least one anatomical structure, and
- an HPI mean of said at least one anatomical structure.

The method 100 may further comprise a step of providing clinical information about each patient, so that the training steps 130 and/or 150 may be further performed on patients clinical information.

Using supplementary features such as morphological and/or radiomics features to train at least one of the 2D model and 3D model allows increasing the robustness of the model.

It is to be appreciated that the 2D machine learning model and/or the 3D machine learning model according to the present disclosure may be based on a deep neural network which can be a convolutional neural network, and vice versa.

Figure 2:
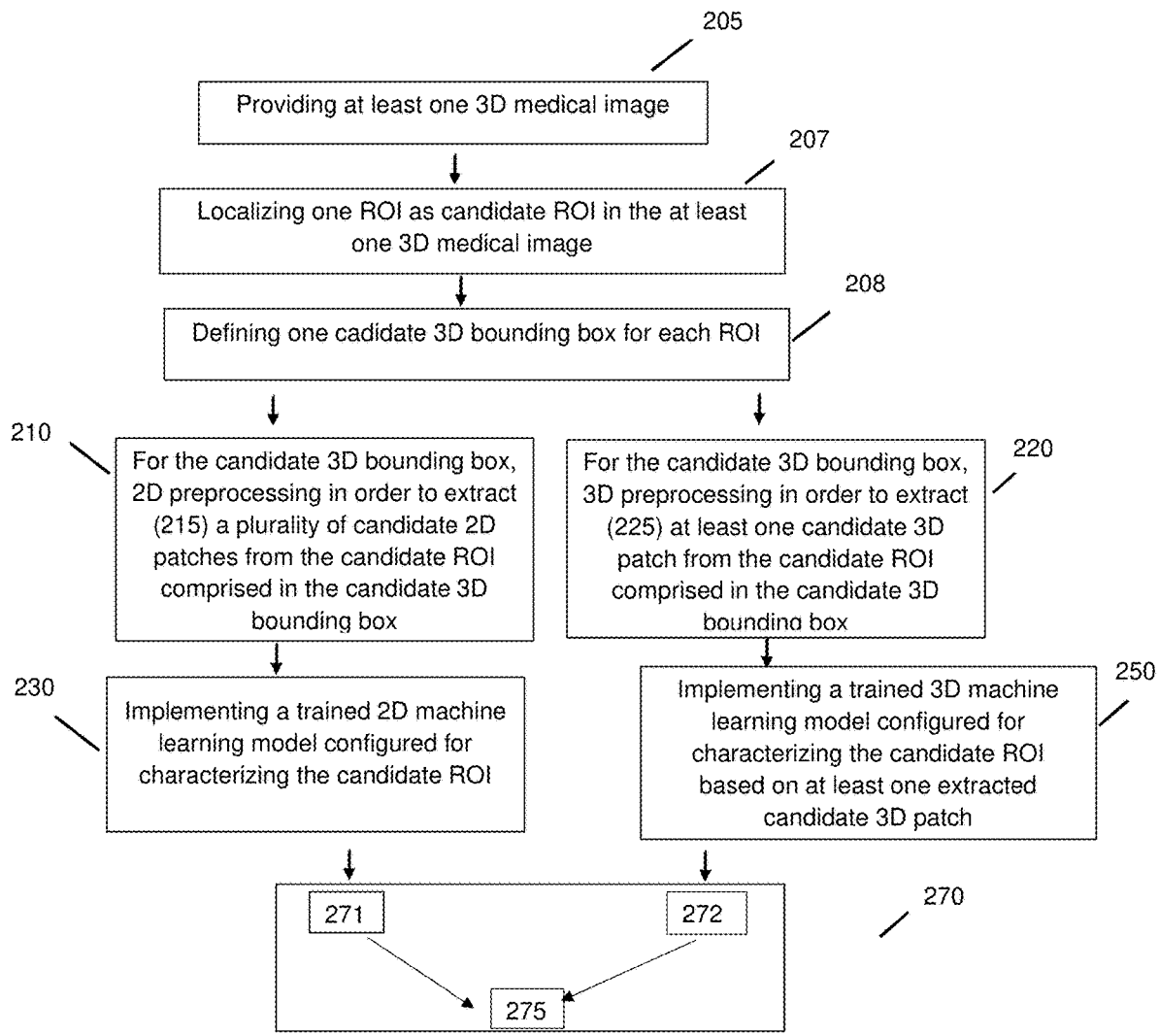
FIG. 2 is a flowchart according to some examples of the method according to the second aspect of the present disclosure.

FIG. 2 shows a flowchart of an embodiment of the second aspect of the present invention.

According to its second aspect, the invention provides a method 200 for characterizing one Region Of Interest ROI based on at least one 3D medical image by applying a trained machine learning model.

The method 200 comprises the steps of:
- Providing 205 said at least one 3D medical image, and
- Localizing 207 one ROI as candidate ROI in said at least one 3D medical image.

Steps 205 and 207 may further be detailed as the above detailed steps 105 and 107.

In some examples, one ROI is localized each time for characterization. The localization step 207 may be repeated iteratively to localize one new ROI each time for characterization.

The method 200 further comprises the steps of:
- For the candidate ROI, defining 208 one candidate 3D bounding box by a set of 6 extreme coordinates (Xmin, Xmax,Ymin,Ymax,Zmin,Zmax).

On one hand, the method 200 further comprises the steps of:
- For the candidate 3D bounding box, 2D preprocessing 210 in order to extract a plurality of candidate 2D patches from the candidate ROI comprised in the candidate 3D bounding box, and
- Implementing 230 a trained 2D machine learning model configured for characterizing a ROI, here the candidate ROI.

Said trained 2D machine learning model may have been trained by implementing the method 100 for generating a machine learning model according to the first aspect of the invention.

On the other hand, the method 200 further comprises the steps of:

For the candidate 3D bounding box, 3D preprocessing 220 in order to extract at least one candidate 3D patch from the candidate ROI comprised in the candidate 3D bounding box, and Implementing 250 a trained 3D machine learning model configured for characterizing a ROI, here the candidate ROI, based on said at least one extracted candidate 3D patch.

Said trained 3D machine learning model may have been trained by implementing a method 100 for generating a machine learning model according to the first aspect of the invention.

Advantageously, the method 200 is such that the step of 2D preprocessing 210 comprises at least: extracting 215 a plurality of K candidate 2D patches as contiguous and parallel slices with respect to a single predetermined plane.

Each 2D patch of the plurality of K 2D patches are obtained without any resampling.

This way the extracted 2D patches can not only cover the integrality of the original data, but also reflect the reality without providing altered information caused by the resampling operation.

As in method 100, the single predetermined plane is parallel to one of the following three planes: the sagittal plane, the coronal plane and the axial plane. More preferably, said single predetermined plane is parallel to the plane having the best resolution. Further preferably, said single predetermined plane is parallel to the axial plane. Thus, the candidate ROI may be better depicted by axial viewed patches.

This way, the diagnosis of the ROI can be precisely made not only for small (spiculated) ROIs by taking consideration of the ROI's morphological characteristics but also for large ROIs by taking consideration of the ROI's size.

Thus, not only the extracted 2D patches cover the integrality of the original data, but also the extracted 2D patches can reflect the reality since without any resampling. The as-comprehensive-as-possible and faithful extraction of the 3D medical image to be inputted to machine learning models for characterizing the ROI will lead to improved accuracy of the characterization (prediction).

Said step of 2D preprocessing 210 may further comprise, before said step of extracting 215 a plurality of K candidate 2D patches, a step of extracting 211 2D ROI coordinates by calculating coordinates of centers of the candidate ROI in axial view of the candidate 3D bounding box (Xmin,Xmax, Ymin,Ymax,Zmin,Zmax). Each center may be defined for example by coordinates ((Xmin+Xmax)/2, (Ymin+Ymax)/2), for all Z in the interval [Zmin, Zmax]. Furthermore, said step of extracting 215 a plurality of K candidate 2D patches may comprise cropping, contiguously along the z-axis, a plurality of K candidate 2D patches of dimensions P×Q, for example with P=Q=64.

If needed, said step of 2D preprocessing 210 may further comprise a step of 2D voxel values normalization 213. This normalization step 213 may be implemented before or after said step of extracting 215 a plurality of K candidate 2D patches and/or may concern normalization of luminance attenuation (HU) of the concerned pixels or voxels. More particularly, the step of 2D voxel values normalization 213 may involve a clip of values of voxels (or pixels since we talk about 2D patches) between two predefined minimal and maximal values, then a transformation by applying a predefined affine function to the values of voxels of the candidate 2D patches. If step 215 is implemented before step 213, then step 213 only needs to be applied on the candidate 3D image from which the K candidate 2D patches are to be extracted 125. If step 213 is implemented before step 215, then it is necessary to normalize the luminance attenuation (HU) on all candidate 2D patches.

Thus, following the step of extracting 215 a plurality of K candidate 2D patches, a plurality of normalized and resampled candidate 2D patches may be achieved, with said normalized and resampled candidate 2D patches being usable for implementing 230 said trained 2D machine learning model.

The aforementioned step of 3D preprocessing 220 in order to extract at least one candidate 3D patch from the candidate ROI may:

comprise a step of extracting 225 at least one candidate 3D patch of the candidate ROI, and prior to the step of extracting 225 at least one candidate 3D patch of the candidate ROI, further comprise a step of extracting 221 3D ROI coordinates by calculating the coordinates of center of the candidate ROI. The candidate ROI center may be for example defined by coordinates ((Xmin+Xmax)/2, (Ymin+Ymax)/2, (Zmin+Zmax)/2).

More particularly, the step of extracting 225 at least one candidate 3D patch may comprise cropping, around the center coordinates of the candidate ROI, a candidate 3D patch of dimensions P×Q×R, for example with P=Q=R=64.

As for said 3D preprocessing step 120 according to the first aspect of the invention, said step of 3D preprocessing 220 according to the second aspect of the invention may further comprise a step of 3D voxel values normalization 223 and/or a step of 3D volume resampling 222 of said at least one 3D image wherein a candidate ROI has been localized 207.

The step of 3D voxel values normalization 223 may be implemented before or after said extracting step 225. More particularly, the step of 3D voxel values normalization 223 may involve a clip of values of voxels between two predefined minimal and maximal values, then a transformation by applying a predefined affine function to the values of voxels of the candidate 3D patch.

The step of 3D volume resampling 222 of said at least one 3D image wherein a candidate ROI has been localized 207 may be implemented before said step of extracting 225 at least one candidate 3D patch. The step of 3D volume resampling 122 may be configured in order to achieve an isometric spacing and/or a 0.65 mm×0.65 mm×0.65 mm resolution.

Thus, following the step of extracting 225 at least one candidate 3D patch, a normalized and resampled candidate 3D patch may be achieved, with said normalized and resampled candidate 3D patch being usable for implementing 250 said trained 3D machine learning model.

Then the method 200 comprises the step of:

Ensembling 270 a plurality of 2D diagnosis scores provided by implementing said trained 2D machine learning model and a plurality of 3D diagnosis score provided by implementing said trained 3D machine learning model in order to output one overall score per said candidate ROI.

Then the step of ensembling 270 takes advantages of the numerous implementations of said trained 2D and 3D machine learning models by potentially comprising:

a step of max-pooling 271 the N series of K candidate 2D diagnosis scores as computed for said plurality of extracted candidate 2D patches, and a step of pooling 272 the M series of least one candidate 3D diagnosis scores for each ROI as computed for said at least one extracted candidate 3D patch.

In some examples, the step of max-pooling 271 the N series of K candidate 2D diagnosis scores as computed for said plurality of extracted candidate 2D patches further comprise:

for each series j of said N series of K candidate 2D diagnosis scores, a step of generating one maximum candidate 2D diagnosis score Sj by selecting, from said K candidate 2D diagnosis scores, the diagnosis score having the maximum value thus achieving one candidate maximum 2D diagnosis score per series for N series, and wherein the trained 2D machine learning model used for each series j of said N series is different from each other, preferably having different weights.

It is advantageous to have a plurality of K 2D patches extracted and inputted into the 2D machine learning model, which allows to obtain multiple outputs, e.g. diagnostic scores, so that a highest score may be selected corresponding to the ROI of highest interest for diagnosis (max-pooling). For example, the highest score may mean that the ROI has higher chance of being diagnosed malignancy or cancerous in a specific case.

It is further advantageous to use different 2D machine models with different weights as this can increase the robustness of the predictions.

The step of ensembling 270 may further comprise a step of outputting 275 one overall score per said candidate ROI by pooling N 2D diagnostic scores of step 271 and M 3D diagnostic scores of step 272 together. Thus one overall score per said candidate ROI is achieved.

As explained above, the pooling is particularly advantageous in the context of the present disclosure as it allows to highlight the high or low value while reducing the uncertainty. Pooling methods do not restrict however to averaging scores, as it can also be profitable to use other methods to derive one score from the 2D and 3D scores (e.g. XGBoost, weighted averages, etc.).

In order to enhance again robustness of the method 200, this latter may further comprise a step of, for the candidate ROI, extracting 260 morphological features of said candidate ROI based on 3D medical image and by using morphoradiomics features extractors. Then the step of ensembling 270 may comprise ensembling the N 2D diagnosis scores from the 2D model, the M 3D diagnosis scores from the 3D model, and at least one of the morphological and/or radiomics features as extracted 260. The here concerned morphological features may be detailed in the same way than those detailed above in relation with the method 100 according to the first aspect of the invention.

Using morphological and/or radiomics features in addition to the 2D diagnosis scores and 3D diagnosis scores to characterize the candidate ROI will further reinforce the robustness of the prediction.

The embodiments and aspects of the here detailed disclosure may be described and illustrated in conjunction with systems, devices and methods which are meant to be exemplary and illustrative, not limiting in scope. Specific configurations and details may be set forth in order to provide an understanding of the disclosure. However, it should be apparent to one skilled in the art that the disclosure may be practiced without some of the specific details being presented herein. Furthermore, some well-known steps or components may be described only generally, or even omitted, for the sake of illustrative clarity.

Some processes may be presented and described in a series (sequence) of steps. It should be understood that the sequence of steps is exemplary, and that the steps may be performed in a different order than presented, some steps which are described may be omitted, and some additional steps may be omitted from the sequence and may be described elsewhere.

Reference may be made to disclosures of prior patents, publications and applications. Some text and drawings from those sources may be presented herein, but may be modified, edited or commented to blend more smoothly with the disclosure of the present application. Citation or identification of any reference should not be construed as an admission that such reference is available as prior art to the disclosure.

The methods described herein may be implemented on any form of computer or computers. The components thereof may be implemented as dedicated applications or in client-server architectures, including a web-based architecture, and can include functional programs, codes, and code segments. Any of the computers may comprise a processor, a memory for storing program data and executing it, a permanent storage such as a disk drive, a communication port for handling communications with external devices, and user interface devices, including a display, keyboard, mouse, etc. When some software or algorithms are involved, they may be stored as program instructions or computer readable codes executable on the processor on a computer-readable media such as read-only memory (ROM), random-access memory (RAM), CD-ROMs, magnetic tapes, floppy disks, and optical data storage devices. The computer readable recording medium can also be distributed over network coupled computer systems so that the computer readable code is stored and executed in a distributed fashion. This media can be read by the computer, stored in the memory, and executed by the processor.

For the purposes of promoting an understanding of the principles of various embodiments of the disclosure, reference has been made to a preferred embodiment illustrated in the drawings, and specific language has been used to describe this embodiment. However, no limitation of the scope of the disclosure is intended by this specific language, and the disclosure should be construed to encompass all embodiments that would normally occur to one of ordinary skill in the art.

The disclosure may be described in terms of functional block components and various processing steps. Such functional blocks may be realized by any number of hardware and/or software components configured to perform the specified functions. For example, the present disclosure may employ various integrated circuit components, e.g., memory elements, processing elements, logic elements, look-up tables, and the like, which may carry out a variety of functions under the control of one or more microprocessors or other control devices. Similarly, where the elements of the present disclosure are implemented using software programming or software elements the present disclosure may be implemented with any programming or scripting language such as C, C++, Java, Python, assembler, or the like, with the various algorithms being implemented with any combination of data structures, objects, processes, routines or other programming elements. Functional aspects may be implemented in algorithms that execute on one or more processors. Furthermore, the present disclosure could employ any number of conventional techniques for electronics configuration, signal processing and/or control, data processing and the like.

What is claimed is:

1. A method for generating a neural network for characterizing a plurality of Regions Of Interest ROIs based on a plurality of 3D medical images, comprising the steps of:

Providing said plurality of 3D medical images and

Localizing a plurality of ROIs in said plurality of 3D medical images, and for each ROI, defining a 3D bounding box by a set of 6 extreme coordinates (Xmin, Xmax,Ymin,Ymax,Zmin,Zmax), and On one hand:

For each defined 3D bounding box, 2D preprocessing in order to extract a plurality of Ki 2D patches from each ROI comprised in said 3D bounding box, and Training a 2D neural network based on the extracted 2D patches, On the other hand:

For each defined 3D bounding box, 3D preprocessing in order to extract at least one 3D patch from each ROI comprised in said 3D bounding box, and Training a 3D neural network for characterizing said plurality of ROIs based on the extracted 3D patches for the plurality of ROIs, wherein the step of 2D preprocessing comprises at least extracting a plurality of Ki 2D patches as contiguous and parallel slices with respect to a single predetermined plane, and wherein the 2D neural network is configured to be trained for characterizing the plurality of ROIs based on the extracted plurality of 2D patches for the plurality of ROIs.

2. The method according to claim 1, wherein said single predetermined plane is parallel to one of the following three planes: the sagittal plane, the coronal plane and the axial plane, and preferably be parallel to the plane having the best resolution, and further preferably parallel to the axial plane.

3. The method according to claim 1, wherein said step of 2D preprocessing further comprises, before said step of extracting a plurality of Ki 2D patches, a step of extracting 2D ROI coordinates by calculating coordinates of centers of each ROI in axial view of each bounding box (Xmin,Xmax, Ymin,Ymax,Zmin,Zmax), with each center being defined for example by coordinates ((Xmin+Xmax)/2, (Ymin+ Ymax)/2), for all Z in [Zmin, Zmax].

4. The method according to claim 3, wherein said step of extracting a plurality of Ki 2D patches comprises cropping, contiguously along the z-axis, a plurality of 2D patches of dimensions P×Q, for example with P=Q=64.

5. The method according to claim 1, wherein said step of 2D preprocessing further comprises a first step of 2D voxel values normalization, this latter being implemented before or after said step of extracting a plurality of Ki 2D patches.

6. The method according to claim 1, wherein said step of 3D preprocessing:

comprises a step of extracting at least one 3D patch of each ROI, and prior to the step of extracting at least one 3D patch of each ROI, further comprises a step of extracting 3D ROI coordinates by calculating the coordinates of center of each ROI, with each ROI center being for example defined by coordinates ((Xmin+Xmax)/2, (Ymin+ Ymax)/2, (Zmin+Zmax)/2).

7. The method according to claim 6, wherein the step of extracting at least one 3D patch comprises cropping, around the center coordinates of each ROI, a 3D patch of dimensions P×Q×R, for example with P=Q=R=64.

8. The method according to claim 5, wherein said step of 3D preprocessing further comprises, before said step of extracting at least one 3D patch, a step of 3D volume resampling of each 3D image wherein a ROI has been localized.

9. The method according to claim 1, wherein the step of 2D training comprises:

an initialization step of said 2D neural network, and a continued training step of said 2D neural network, wherein, with said 2D neural network being designed for computing diagnosis score based on one 2D patch, the initialization step comprises initializing weights of said 2D neural network based on at least one among random determination of said weights and predetermined weights, and wherein the continued training step comprises:

i. for each mini-batch of all the extracted patches of the plurality of ROIs, a computing step of diagnosis score using 2D neural network, wherein the mini-batch is selected randomly, ii. for each previously computed diagnosis score, a computing step of error estimation made by the 2D neural network, iii. an updating step of the weights using a gradient-based method, iv. repeating steps i to iii until a predefined stopping condition is reached, thus achieving a trained 2D neural network with optimized weights.

10. The method according to claim 1, wherein the 3D training step comprises:

an initialization step of said 3D neural network, and a continued training step of said 3D neural network, wherein, with said 3D neural network being designed for computing diagnosis score based on one 3D patch, the initialization step comprises initializing weights of said 3D neural network based on at least one among random determination of said weights and predetermined weights, and wherein the continued training step comprises:

i. for each mini-batch of all the extracted patches of the plurality of ROIs, a computing step of diagnosis score using 3D neural network, wherein the mini-batch is selected randomly, ii. for each previously computed diagnosis score, a computing step of error estimation made by the 3D neural network, iii. an updating step of the weights using a gradient-based method, iv. repeating steps i to iii until a predefined stopping condition is reached, thus achieving a trained 3D neural network with optimized weights.

11. A non-transitory computer readable medium storing instructions which, when implemented by at least one digital processing device, performs at least ones among the steps of the method according to claim 1.

12. A method for characterizing a Region Of Interest ROI based on at least one 3D medical image, comprising the steps of:

Providing said at least one 3D medical image, and

Localizing one ROI as candidate ROI in said at least one 3D medical image, and

For candidate ROI, defining one candidate 3D bounding box by a set of 6 extreme coordinates, and On one hand:

For the candidate 3D bounding box, 2D preprocessing in order to extract a plurality of candidate 2D patches from the candidate ROI comprised in the candidate 3D bounding box, and Implementing a trained 2D neural network configured for characterizing the candidate ROI, On the other hand:
- For the candidate 3D bounding box, 3D preprocessing in order to extract at least one candidate 3D patch from the candidate ROI comprised in the candidate 3D bounding box, and
- Implementing a trained 3D neural network configured for characterizing the candidate ROI based on at least one extracted candidate 3D patch, then
- Ensembling a plurality of 2D diagnosis scores provided by said trained 2D neural network and a plurality of 3D diagnosis score provided by said trained 3D neural network in order to output one overall score per said candidate ROI, wherein the step of 2D preprocessing comprises at least extracting a plurality of K candidate 2D patches as contiguous and parallel slices with respect to a single predetermined plane, and
wherein the step of implementing the trained 2D neural network is performed based on the extracted plurality of candidate 2D patches.

13. The method according to claim 12, wherein said trained 2D and 3D neural networks have been trained by implementing a method for generating a neural network according to claim 1.

14. The method according to claim 12, wherein said single predetermined plane is parallel to one of the following three planes: the sagittal plane, the coronal plane and the axial plane, and preferably be parallel to the plane having the best resolution, and further preferably parallel to the axial plane.

15. The method according to claim 12, wherein said step of 2D preprocessing further comprises, before said step of extracting a plurality of K candidate 2D patches, a step of extracting 2D ROI coordinates by calculating coordinates of centers of the candidate ROI in axial view of the candidate 3D bounding box, with each center being defined for example by coordinates ((Xmin+Xmax)/2, (Ymin+Ymax)/2), for all Z in [Zmin, Zmax].

16. The method according to claim 15, wherein said step of extracting a plurality of K candidate 2D patches comprises cropping, contiguously along the z-axis, a plurality of K candidate 2D patches of dimensions P×Q, for example with P=Q=64.

17. The method according to claim 12, wherein said step of 2D preprocessing further comprises a second step of 2D voxel values normalization, this latter being implemented before or after said step of extracting a plurality of K candidate 2D patches.

18. The method according to claim 12, wherein said step of 3D preprocessing:
- comprises a step of extracting at least one candidate 3D patch of the candidate ROI, and
- prior to the step of extracting at least one candidate 3D patch of the candidate ROI, further comprises a step of extracting 3D ROI coordinates by calculating the coordinates of center of the candidate ROI, with the candidate ROI center being for example defined by coordinates ((Xmin+Xmax)/2, (Ymin+Ymax)/2, (Zmin+Zmax)/2).

19. The method according to claim 18, wherein the step of extracting at least one candidate 3D patch comprises cropping, around the center coordinates of the candidate ROI, a candidate 3D patch of dimensions P×Q×R, for example with P=Q=R=64.

20. The method according to claim 18, wherein said step of 3D preprocessing further comprises, before said step of extracting at least one candidate 3D patch of the candidate ROI, a 3D volume resampling of each 3D image wherein the candidate ROI has been localized.

21. The method according to claim 12, wherein the step of implementing the trained 2D neural network is performed N times based on the plurality of K extracted candidate 2D patches in order to compute, each time, K candidate diagnosis scores for one candidate ROI, thus achieving K candidate 2D diagnosis scores for each one series of N series.

22. The method according to claim 12, wherein the step of implementing the trained 3D neural network is performed M times based on the at least one extracted candidate 3D patch in order to compute each time at least one candidate diagnostic score for one candidate ROI, thus achieving at least one candidate 3D diagnosis scores for each series of M series.

23. The method according to claim 21, wherein the step of ensembling comprises:
- a step of pooling the N series of at least one candidate 2D diagnosis score for each ROI as computed N times for said plurality of K extracted candidate 2D patches by max-pooling, with said step of max-pooling comprising, for each series j of said N series of K candidate 2D diagnosis scores, a step of generating one maximum candidate 2D diagnosis score Sj by selecting, from said K candidate 2D diagnosis scores, the diagnosis score having the maximum value thus achieving one candidate maximum 2D diagnosis score per series for N series, wherein the trained 2D neural network used for each series j of said N series is different from each other, preferably having different weights, and
- a step of pooling the M series of at least one candidate 3D diagnosis scores for each ROI as computed for said at least one extracted candidate 3D patch.

24. The method according to claim 23, wherein the step of ensembling further comprises a step of outputting one overall score per said candidate ROI by pooling N 2D diagnostic scores of step and M 3D diagnostic scores of step together.

25. Method according to claim 1, wherein the 3D medical images comprise at least one among: Computed Tomography (CT) images and Magnetic Resonance Imaging (MRI) images.

26. Method according to claim 12, wherein the 3D medical images comprise at least one among: Computed Tomography (CT) images and Magnetic Resonance Imaging (MRI) images.

27. A non-transitory computer readable medium storing instructions which, when implemented by at least one digital processing device, performs the steps of the method according to claim 12.

* * * * *